(12) United States Patent
Li

(10) Patent No.: US 8,345,349 B2
(45) Date of Patent: Jan. 1, 2013

(54) COMPACT OPTICAL RESONATORS

(75) Inventor: Jingjing Li, Palo Alto, CA (US)

(73) Assignee: Hewlett-Packard Development Company, L.P., Houston, TX (US)

(*) Notice: Subject to any disclaimer, the term of this patent is extended or adjusted under 35 U.S.C. 154(b) by 649 days.

(21) Appl. No.: 12/472,600

(22) Filed: May 27, 2009

(65) Prior Publication Data

US 2010/0303123 A1    Dec. 2, 2010

(51) Int. Cl.
- *G02F 1/01* (2006.01)
- *G01N 21/39* (2006.01)
- *H01S 3/131* (2006.01)
- *H01S 3/14* (2006.01)

(52) U.S. Cl. .................. 359/342; 359/247; 356/432

(58) Field of Classification Search .............. 359/344, 359/248, 342, 247; 372/39, 66, 92, 705; 356/432

See application file for complete search history.

(56) References Cited

U.S. PATENT DOCUMENTS

| | | | | |
|---|---|---|---|---|
| 3,951,513 | A * | 4/1976 | Masi | 385/8 |
| 5,105,301 | A * | 4/1992 | Campi | 359/245 |
| 5,307,200 | A * | 4/1994 | Yoshida | 359/248 |
| 5,424,559 | A * | 6/1995 | Kasahara | 257/21 |
| 6,188,511 | B1 * | 2/2001 | Marcenac et al. | 359/344 |
| 7,123,407 | B2 * | 10/2006 | Byun et al. | 359/344 |
| 7,274,010 | B2 * | 9/2007 | Matsuda et al. | 250/214 LA |
| 7,352,941 | B2 * | 4/2008 | Bratkovski et al. | 385/129 |
| 2004/0032647 | A1 * | 2/2004 | Wasserbauer | 359/344 |
| 2006/0024066 | A1 * | 2/2006 | Fujiwara et al. | 398/183 |
| 2008/0267243 | A1 * | 10/2008 | Wang et al. | 372/69 |
| 2012/0033283 | A1 * | 2/2012 | Halsema | 359/245 |

OTHER PUBLICATIONS

G. Dolling, M. Wegener, C. M. Soukoulis, and S. Linden, "Negative-index metamaterial at 780 nm wavelength," Opt. Lett. 32, 53-55 (2007) http://www.opticsinfobase.org/abstract.cfm?URI=ol-32-1-53.*

Gunnar Dolling, Christian Enkrich, Martin Wegener, Costas M. Soukoulis, and Stefan Linden, "Low-loss negative-index metamaterial at telecommunication wavelengths," Opt. Lett. 31, 1800-1802 (2006) http://www.opticsinfobase.org/abstract.cfm?URI=ol-31/12/1800.*

Pendry, et. al., "Reversing Light with Negative Refraction," Physics Today, 57 [6] 37-43 (Jun. 2004).*

Alu, A.; Bilotti, F.; Engheta, N.; Vegni, L.; , "Subwavelength, Compact, Resonant Patch Antennas Loaded With Metamaterials," Antennas and Propagation, IEEE Transactions on , vol. 55, No. 1, pp. 13-25, Jan. 2007 doi: 10.1109/TAP.2006.888401 URL: http://ieeexplore.ieee.org/stamp/stamp.jsp?tp=&arnumber=4052597&isnumber=4052595.*

Nader Engheta; Ziolkowski, R.W.; , "A positive future for double-negative metamaterials," Microwave Theory and Techniques, IEEE Transactions on , vol. 53, No. 4, pp. 1535-1556, Apr. 2005 doi: 10.1109/TMTT.2005.845188 URL: http://ieeexplore.ieee.org/stamp/stamp.jsp?tp=&arnumber=1420795&isnumber=30700.*

(Continued)

*Primary Examiner* — Isam Alsomiri
*Assistant Examiner* — Ari M Diacou

(57) ABSTRACT

Various embodiments of the present invention are directed to compact, sub-wavelength optical resonators. In one aspect, an optical resonator comprises two approximately parallel reflective structures positioned and configured to form a resonant cavity. The resonator also includes a fishnet structure disposed within the cavity and oriented approximately parallel to the reflective structures. The resonant cavity is configured with a cavity length that can support resonance with electromagnetic radiation having a fundamental wavelength that is more than twice the cavity length.

13 Claims, 15 Drawing Sheets

OTHER PUBLICATIONS

Engheta, N.; , "An idea for thin subwavelength cavity resonators using metamaterials with negative permittivity and permeability," Antennas and Wireless Propagation Letters, IEEE , vol. 1, no., pp. 10-13, 2002 doi: 10.1109/LAWP.2002.802576 URL: http://ieeexplore.ieee.org/stamp/stamp.jsp?tp=&arnumber=1020308&isnumber=21952.*

M. Kafesaki, I. Tsiapa, N. Katsarakis, Th. Koschny, C. M. Soukoulis, and E. N. Economou. Left-handed metamaterials: The fishnet structure and its variations. Phys. Rev. B 75, 235114 (2007). URL: http://link.aps.org/doi/10.1103/PhysRevB.75.235114 DOI: 10.1103/PhysRevB.75.235114.*

Wikipedia contributors. Laser construction. Wikipedia, The Free Encyclopedia. May 16, 2008, 12:08 UTC. Available at: http://en.wikipedia.org/w/index.php?title=Laser_construction&oldid=212817967. Accessed Aug. 11, 2011.*

Richard W. Ziolkowski, "Ultrathin, metamaterial-based laser cavities," J. Opt. Soc. Am. B 23, 451-460 (2006) http://www.opticsinfobase.org/abstract.cfm?URI=josab-23-3-451.*

Shumin Xiao, Uday K. Chettiar, Alexander V. Kildishev, Vladimir P. Drachev, and Vladimir M. Shalaev, "Yellow-light negative-index metamaterials," Opt. Lett. 34, 3478-3480 (2009) http://www.opticsinfobase.org/ol/abstract.cfm?URI=ol-34-22-3478.*

* cited by examiner

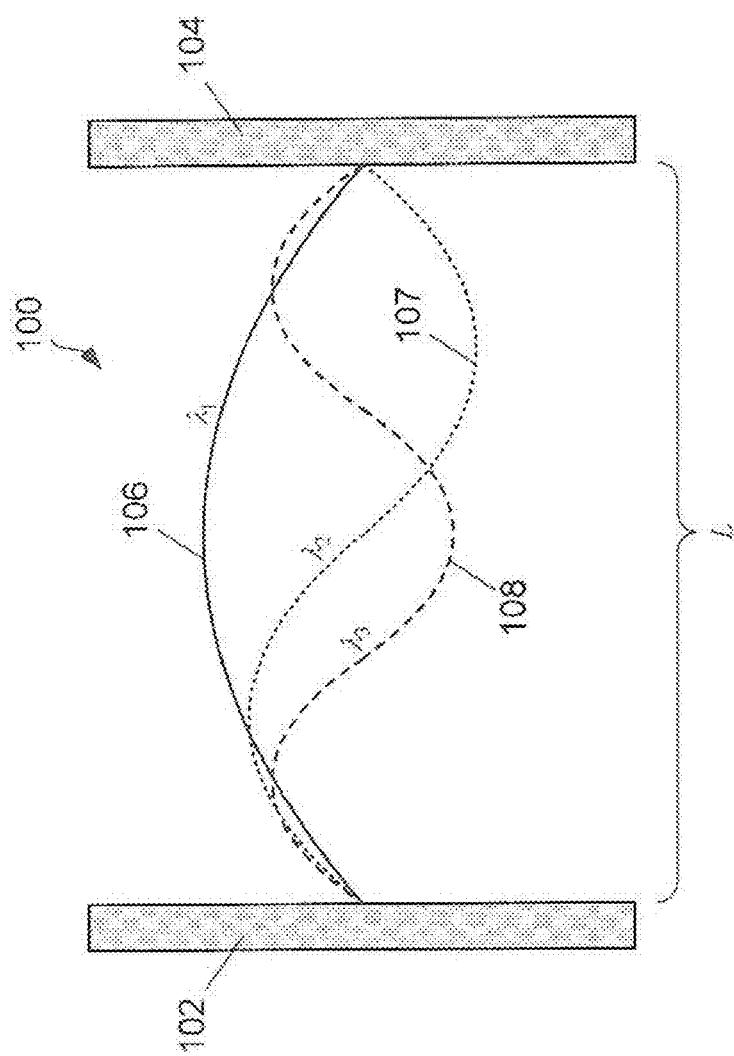

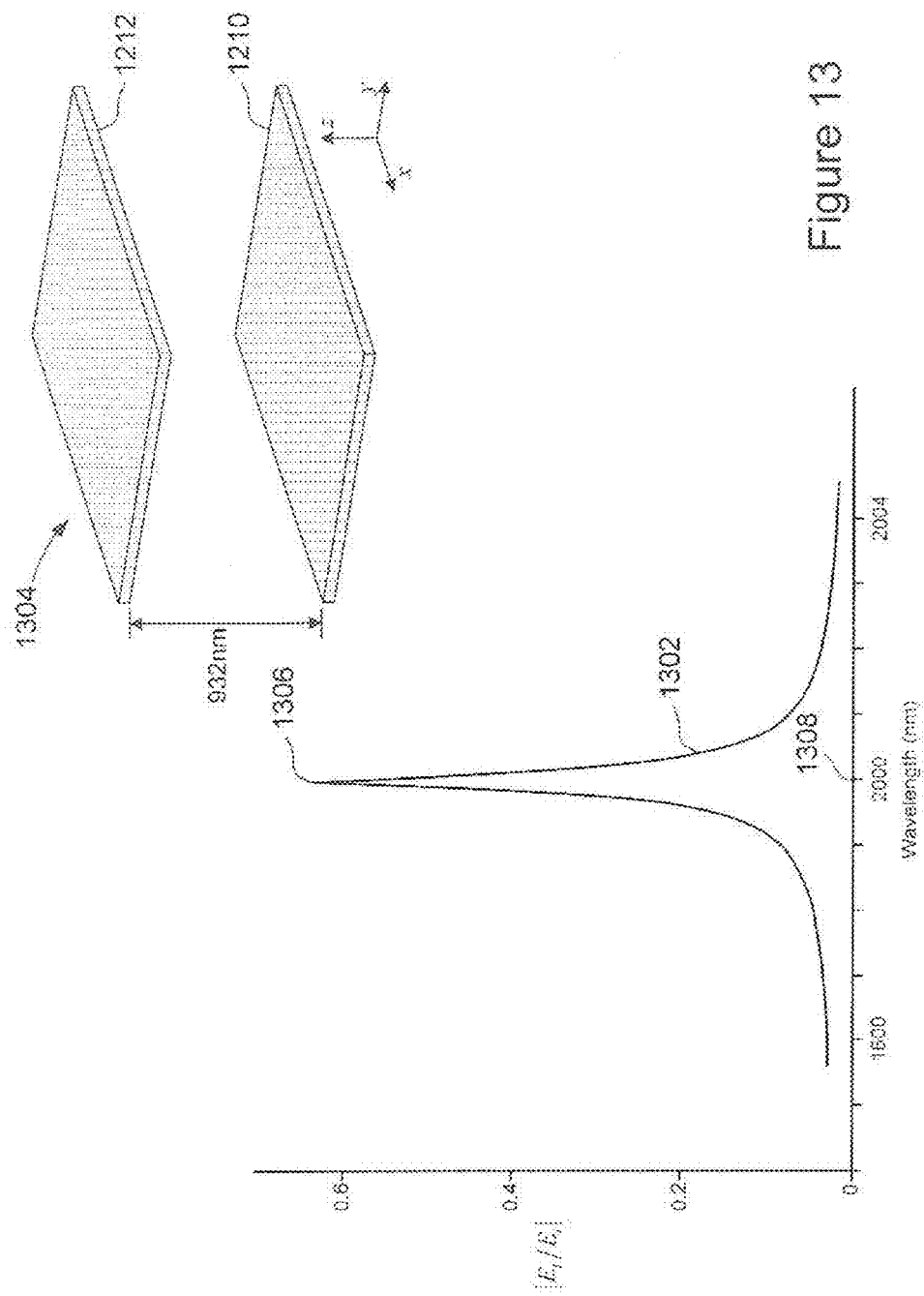

COMPACT OPTICAL RESONATORS

TECHNICAL FIELD

Embodiments of the present invention relate to optical resonators, in particular, to compact optical resonators including a unit layer of material.

BACKGROUND

An optical resonator is an arrangement of optical components that enable a beam of electromagnetic radiation to circulate in a closed path. Optical resonators are a major component of lasers, surrounding a gain medium and providing feedback for laser beam generation. For example, an axial beam of electromagnetic radiation continues to build as it bounces back and forth across the gain medium disposed within an optical resonator. This accounts for the degree of coherence of the output laser beam. Although the gain medium amplifies the wave, the feedback provided by the optical resonator aids in building up a coherent laser beam. Optical resonators have also been adapted for use in optical parametric oscillators and interferometers.

Electromagnetic radiation of appropriate wavelengths bounces back and forth between the mirrors of an optical resonator and takes on a standing-wave configuration determined by the separation distance, L, between the mirrors. This distance L is called the "cavity length." When the mirrors are made of an electric conductor, the optical resonator resonates (i.e., standing waves exists within it) when there is an integer number of half wavelengths spanning the cavity between the mirrors. In other words, electromagnetic radiation resonates in a resonator when $$L = \frac{m\lambda_m}{2}$$

where $\lambda_m$ is the wavelength of the electromagnetic wave that can resonate in the optical resonator. In principle, there are an infinite number of possible oscillatory longitudinal resonator modes, each with a distinctive resonance wavelength $\lambda_m$.

FIG. 1 shows a side view and schematic representation of an exemplary optical resonator 100 comprising mirrors 102 and 104. The mirrors 102 and 104 form a resonant Fabry-Perot cavity with a cavity length L. Curves 106-108 represent three standing waves with resonance wavelengths $\lambda_1$, $\lambda_2$, and $\lambda_3$, respectively, of electromagnetic radiation resonating within the cavity of the optical resonator 100. Curve 106 represents the longest resonance wavelength $\lambda_1$ the resonator 100 can support and is called the "fundamental." In other words, $\lambda_1/2$ is the minimum cavity length L the resonator 100 can be configured with to provide resonance for the fundamental wavelength $\lambda_1$. Curve 107 is the second longest resonance wavelength $\lambda_2$ the resonator 100 can support, and curve 108 is the third longest resonance wavelength $\lambda_3$ the resonator 100 can support.

In recent years, various types of optical resonators have been developed, such as photonic crystal resonators and ring resonators. However, for nearly all of these resonators, the minimum cavity length is about half the fundamental wavelength. Optical resonators that can be configured with sizes and cavity lengths that are smaller than half of the fundamental wavelength are desired.

BRIEF DESCRIPTION OF THE DRAWINGS

FIG. 1 shows a side view and schematic representation of an optical resonator.

FIG. 13 shows a plot of a transmission curve versus wavelength for a Fabry-Perot cavity.

DETAILED DESCRIPTION

Various embodiments of the present invention are directed to compact, sub-wavelength optical resonators. The optical resonators comprise a negative index material disposed between two resonator reflective structures. The cavity length of the optical resonators is considerably shorter than half the fundamental wavelength the optical resonator can support. Optical resonators configured in accordance with embodiments of the present invention can also be operated as optical modulators and sensors.

The detailed description of the present invention is organized as follows. A general description of negative index materials is provided in a first subsection. A description of negative index materials having a fishnet configuration is provided in a second subsection. Optical resonator embodiments are described in a third subsection.

In the following description, the term "optical" refers to classical and/or quantized electromagnetic radiation having wavelengths in the visible and non-visible portions of the electromagnetic spectrum.

Negative Index Materials

Negative index materials ("NIMs"), also called metamaterials, are materials with optical properties resulting from the structure of the material rather than from the chemical composition of the material. Natural materials have positive permeability, $\mu$, and may have positive or negative dielectric permittivity $\in$, depending on the type of conductivity of the material and frequency ranges. In contrast, NIMs have simultaneously negative $\in$ and $\mu$ for certain portions of the electromagnetic spectrum, which results in optical properties that are different from those of ordinary composite materials. The optical properties of NIMs can be appreciated by comparing and contrasting the optical properties of NIMs with the optical properties of ordinary composite materials, as described in *Electrodynamics of Metamaterials*, by A. K. Sarychev and V. M. Shalaev (World Scientific, New York, 2007). For example, consider Maxwell's first-order differential equations for an electromagnetic wave propagating in an ordinary composite material with a time harmonic field as follows:

$$\nabla \times \overline{E} = -j\omega\mu\overline{H}$$

$$\nabla \times \overline{H} = j\omega \in \overline{E}$$

where $\overline{E}$ is the electric field component, $\overline{H}$ is the magnetic field component, $j=\sqrt{-1}$, and $\omega$ is the angular frequency. The solutions of these equations are the plane-wave fields:

$$\overline{E} = \overline{E}_0 \exp(-j\overline{k}_o \cdot \overline{r})$$

$$\overline{H} = \overline{H}_0 \exp(-j\overline{k}_o \cdot \overline{r})$$

Figure 2A:
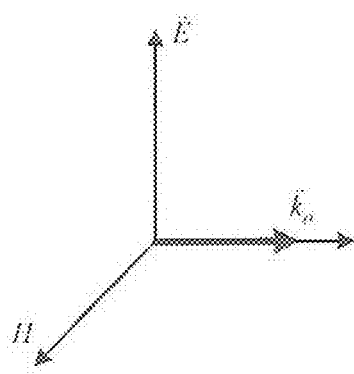
FIGS. 2A-2B show wave and Poynting vector directions for electromagnetic waves propagating in an ordinary right-handed medium.
Figure 2B:
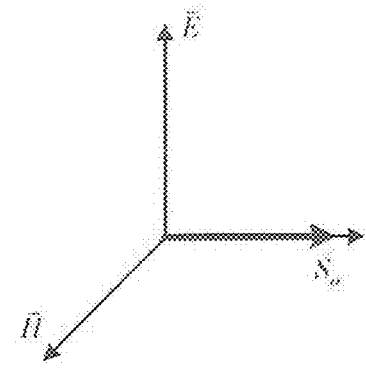
Figure 3A:
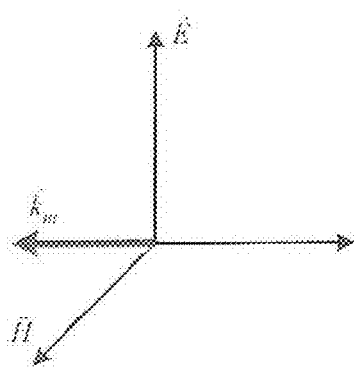
FIGS. 3A-3B show wave and Poynting vector directions for electromagnetic waves propagating in a negative index metamaterial.
Figure 3B:
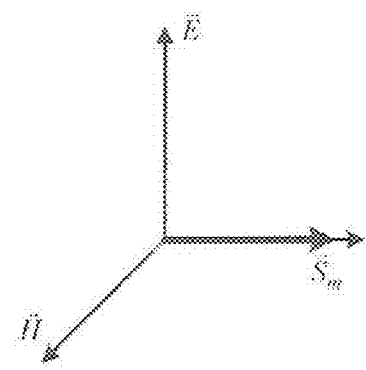

Substituting the plane-wave equations into Maxwell's first order differential equations gives the relations:

$$\overline{k}_o \times \overline{E} = \omega\mu\overline{H}$$

$$\overline{k}_o \times \overline{H} = -\omega \in \overline{E}$$

where $\overline{k}_o$ is a wavevector indicating the direction an electromagnetic wave propagates within a composite material. FIG. 2A shows the spatial relationship and relative orientation of the vectors $\overline{E}$, $\overline{H}$, and $\overline{k}_o$ and reveals that for an ordinary composite material with positive $\in$ and $\mu$, the vectors $\overline{E}$, $\overline{H}$, and $\overline{k}_o$ form an orthogonal, right-handed system of vectors. In addition, the direction of the time-averaged energy flux of the electromagnetic wave is given by the real component of the Poynting vector:

$$\vec{S}_o = \frac{1}{2} \text{Re}(\vec{E} \times \vec{H}^*)$$

which, as shown in FIG. 2B, reveals that the vectors $\overline{E}$, $\overline{H}$, and $\overline{S}_o$ also form an orthogonal, right-handed vector system. In other words, FIGS. 3A and 3B, show that for an electromagnetic wave propagating through a ordinary composite material, the propagation direction identified by the wavevector $\overline{k}_o$ and the direction of the energy carried by the electromagnetic wave identified by the Poynting vector $\overline{S}_o$ are the same.

On the other hand, consider NIMs, where $\in<0$ and $\mu<0$. Maxwell's first order differential equations give the relations:

$$\overline{k}_m \times \overline{E} = -\omega|\mu|\overline{H}$$

$$\overline{k}_m \times \overline{H} = \omega|\in|\overline{E}$$

where $\overline{k}_m$ is a wavevector indicating the direction the phase the electromagnetic wave propagates in a NIM. As shown in FIG. 3A, and in contrast to the composite materials shown in FIG. 2A, for NIMs, the vectors $\overline{E}$, $\overline{H}$, and $\overline{k}_m$ form an orthogonal, left-handed system of vectors. In other words, comparing the directions of the wavefronts represented by the wavevectors $\overline{k}_c$ and $\overline{k}_m$ shown in FIGS. 2A and 3A, respectively, reveals that electromagnetic waves propagate backwards in NIMs for the same orientation of the vectors $\overline{E}$ and $\overline{H}$. Thus, NIMs are also referred to as "left-handed media" or "backward media." However, as shown in FIG. 3B, the Poynting vector $\overline{S}_m$ in a metamaterial is unaffected by the change of sign of $\in$ and $\mu$, and the vectors $\overline{E}$, $\overline{H}$, and $\overline{S}_m$ still form an orthogonal, right-handed system of vectors in a left-handed medium. Therefore, in NIMs, energy and wavefronts travel in opposite directions.

Now consider the refraction of an incident ray at the interface between ordinary and left-handed media. Based on the properties of electromagnetic waves travelling in NIMs described above, it follows that, unlike refraction observed in ordinary media, the angles-of-incidence and refraction have opposite signs. Snell's law in NIMs becomes:

$$\frac{\sin\theta_1}{\sin\theta_2} = \frac{-|k_2|}{|k_1|} \equiv \frac{n_2}{n_1} < 0,$$

where the subscripts 1 and 2 identify ordinary and left-handed media, respectively. Assuming $n_1>0$, from Snell's law it follows that $n_2<0$. That is, the sign of the square root in the definition of the refractive index is chosen to be negative:

$$n_2 = -\sqrt{\in\mu} < 0$$

Hence the term "negative index material" is used to refer to materials having both negative $\in$ and $\mu$.

Figure 4:
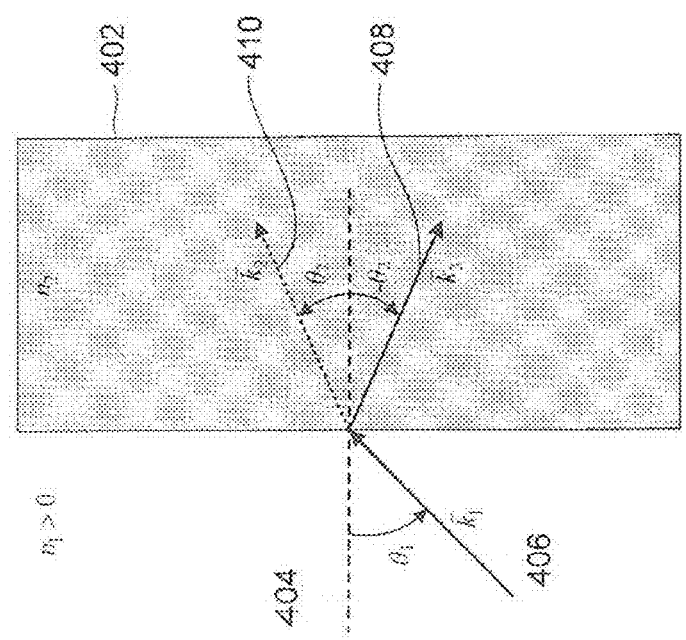
FIG. 4 shows refraction of rays of electromagnetic radiation in an ordinary right-handed medium and a negative index metamaterial.

FIG. 4 shows refraction of rays of electromagnetic radiation in an ordinary right-handed medium and a negative index metamaterial. Dashed line 404 represents a surface normal extending perpendicular to the surface of a medium 402. As shown in FIG. 4, angle $\theta_1$ and wavevector $\overline{k}_1$ 406 represent the angle-of-incidence and direction of a ray of electromagnetic radiation propagating through an ordinary medium with index of refraction $n_1>0$ and is incident on the medium 402. Angle $-\theta_2$ and wavevector $\overline{k}_3$ 408 represent the angle-of-refraction and direction of a refracted ray of electromagnetic radiation propagating within the medium 402 with refractive index $n_2<0$, while angle $\theta_2$ and wavevector $\overline{k}_2$ 410 represent the angle-of-refraction and direction of a refracted ray of electromagnetic radiation propagating within the medium 402 with refractive index $n_2>0$, where $|n_2|>n_1$. Thus, for the medium 402 with a refractive index of $n_2<0$, the incident ray 406 and the refracted ray 408 lie on the same side of the surface normal 404, and for the medium 402 with a refractive index of $n_2>0$, the incident ray 406 and the refracted ray 410 lie on opposite sides of the surface normal 404.

Figure 5:
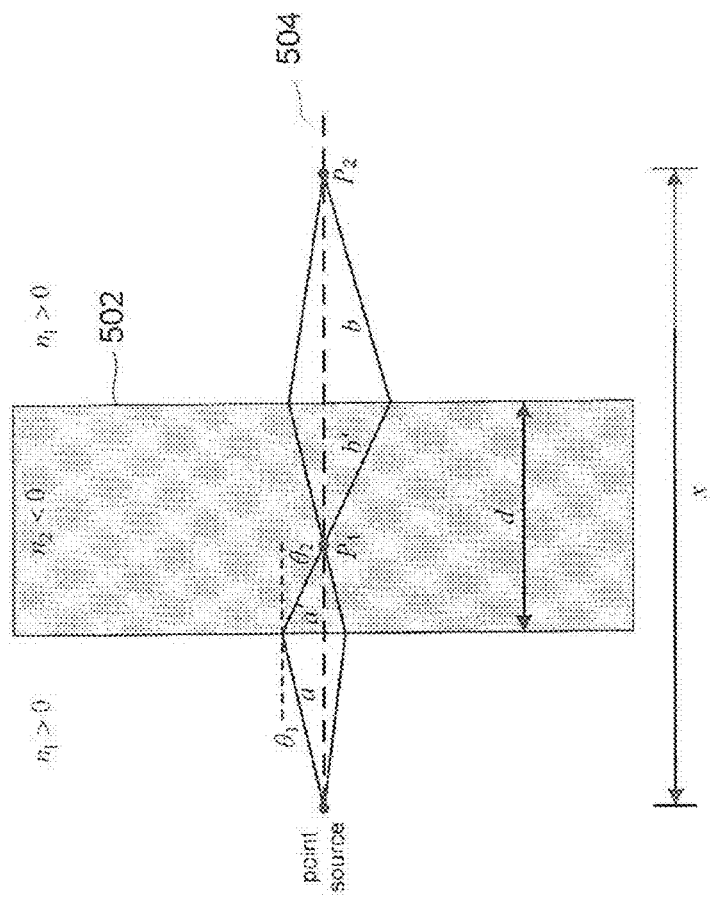
FIG. 5 shows focusing properties of a metamaterial slab for electromagnetic radiation emanating from a point source.

Tracing the paths of optical rays through conventional concave and convex lens made of left-handed media reveals that concave lenses become convergent and convex lens become divergent, thus reversing the behavior of lenses comprising ordinary media. FIG. 5 shows focusing properties of a slab 502 composed of a NIM for electromagnetic radiation emanating from a point source. For incident rays paraxial to an optical axis 504, Snell's law gives:

$$|n| = \frac{|n_2|}{n_1} = \frac{|\sin\theta_1|}{|\sin\theta_2|} \square \frac{|\tan\theta_1|}{|\tan\theta_2|} = \frac{a'}{a} = \frac{b'}{b}$$

where n is the refractive index $n_2$ of the slab 502 relative to refractive index of the surrounding medium $n_1$. As shown in FIG. 5, rays emanating from the point source are focused at two points $P_1$ and $P_2$. Point $P_1$ lies inside the slab 502 and point $P_2$ lies on the side of the slab 502 opposite the point source. The distance from the point source to the second focusing point $P_2$ is given by:

$$x = a + a' + b' + b = d + \frac{d}{|n|}$$

where d is the width of the slab. When n equals −1, the focusing effect is not restricted to paraxial rays, because in this case $|\theta_1|$ equals $|\theta_2|$ for any angle-of-incidence, In fact, when n equals −1, all rays emanating from the point source are focused at two points, the latter point $P_2$ being at a distance 2d from the point source. Thus, unlike slabs comprising ordinary composite materials, NIM slabs can be configured to focus electromagnetic radiation.

Fishnet Structures

Figure 6:
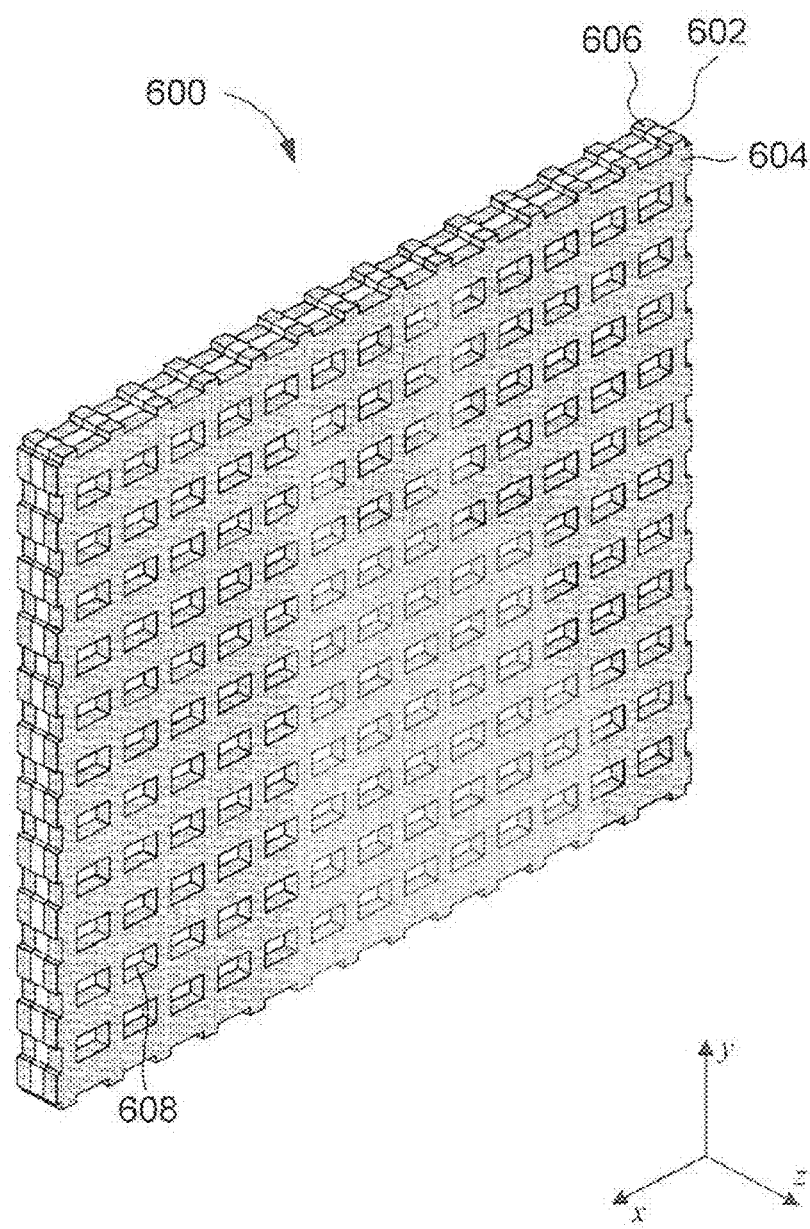
FIG. 6 shows an isometric view of a negative index material fishnet structure configured in accordance with embodiments of the present invention.

FIG. 6 shows an isometric view of a material 600 configured in accordance with embodiments of the present invention. The material 600 is a three layer structure comprising an intermediate layer 602 sandwiched between two conducting layers 604 and 606. The material 600 includes an array of approximately regularly spaced holes, such as hole 608. The array of holes produces a mesh or fishnet appearance. Thus, the material 600 is referred to below as a "fishnet."

Figure 7:
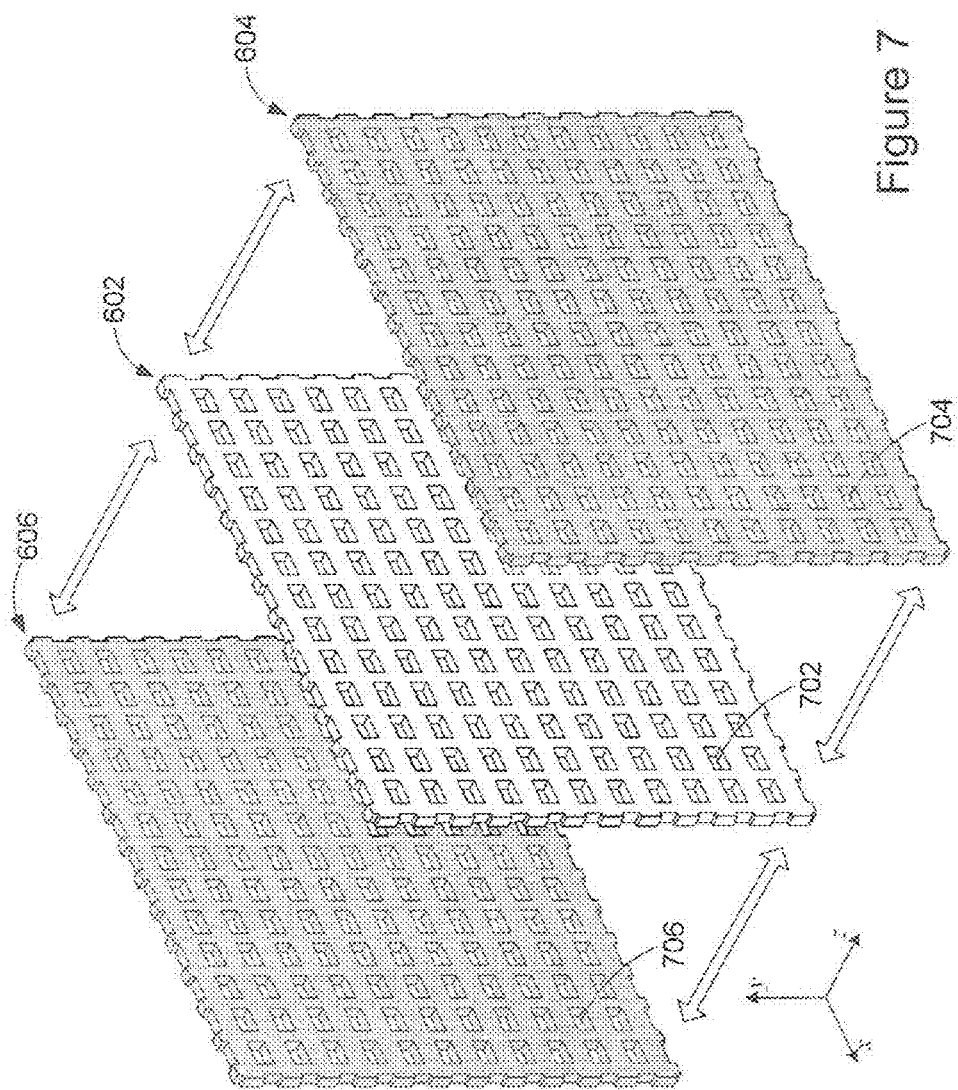
FIG. 7 shows an exploded isometric view of the negative index material fishnet configured in accordance with embodiments of the present invention.

FIG. 7 shows an exploded isometric view of the fishnet 600 configured in accordance with embodiments of the present invention. FIG. 7 reveals an array of approximately regularly spaced rectangular-shaped holes extending through all three of the layers 602, 604, and 606, with the holes in each layer aligned with the holes in the other two layers. For example, holes 702, 704, and 706 in layers 602, 604, and 606, respectively, are aligned, forming the single hole 608 extending through fishnet 600. In certain embodiments, as shown in FIGS. 6 and 7, the holes can be rectangular, and in other embodiments, the holes can be square, elliptical, circular, irregularly shaped, or any other suitable shape.

Figure 8:
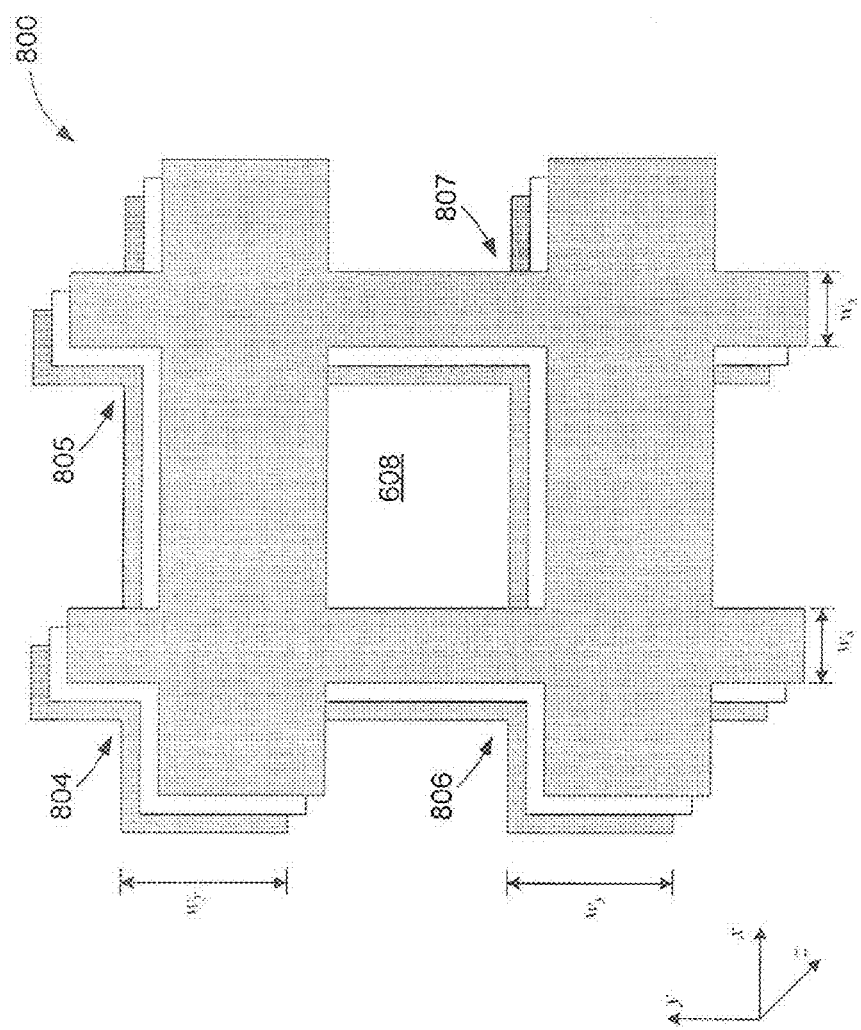
FIG. 8 shows an isometric view and enlargement of four adjacent resonant structures of a negative index material fishnet configured in accordance with embodiments of the present invention.

FIGS. 6 and 7 also reveal that the holes extending in the x-direction are separated by portions of the fishnet 600 that are relatively thinner than portions of the fishnet 600 separating holes extending in the y-direction. FIG. 8 shows an isometric view and enlargement 800 of the fishnet 600 region around the hole 608 in accordance with embodiments of the present invention. As shown in FIG. 8, the width $w_x$ of material separating holes extending in the x-direction is less than the width $w_y$ of material separating holes in extending in the y-direction. The intersections of thin and relatively thicker portions of the fishnet 600 form resonant structures, such as the four adjacent resonant structures 804-807.

The outer layers 604 and 606 can be comprised of silver ("Ag"), gold ("Au"), copper ("Cu"), aluminum ("Al"), platinum ("Pt"), or another suitable electronically conducting metal, or the layers 604 and 606 can be composed of heavily doped semiconductors depending on the wavelength of incident electromagnetic radiation. The intermediate layer 602 can be composed of $SiO_2$, $Al_2O_3$, $TiO_2$, a dielectric polymer, or any other suitable dielectric material.

The fishnet 600, shown in FIGS. 6-8, can be manufactured by any of numerous relatively straightforward processes. For example, the layers 602, 604, and 606 can be deposited using chemical vapor deposition, physical vapor deposition, or the layers can be prefabricated in separate deposition processes and wafer bonded together. In other embodiments, the layers 602, 604, 606 can be formed using a combination of deposition and wafer bonding. The array of holes creating the fishnet appearance can be formed using mechanical nanoimprinting techniques, reactive ion etching, or focused beam milling. The fishnet 600 may be connected to microscale address-wire leads or other electronic leads, through a variety of different methods in order to electronically couple the layers 604 and 606 to electronic devices.

The resonant structures can be configured with dimensions that are smaller than the wavelength λ of electromagnetic radiation incident on the fishnet 600. In certain embodiments, the fishnet 600 can be operated as a NIM over particular wavelength ranges of interest. In particular, the size and shape of the resonant structures can be selected to have an appropriate inductance, resistance, and capacitance response to a wavelength of interest. In addition, the refractive index of the intermediate layer can be adjusted by applying appropriate electronic signals, such as voltages or currents, to the layers 604 and 606. The size and shape of the resonant structures and control over the refractive index of the intermediate layer 602 enables the fishnet 600 to be configured and operated as a NIM over particular wavelength ranges of interest and shift the transmission phase of electromagnetic radiation transmitted through the fishnet 600.

Figure 9:
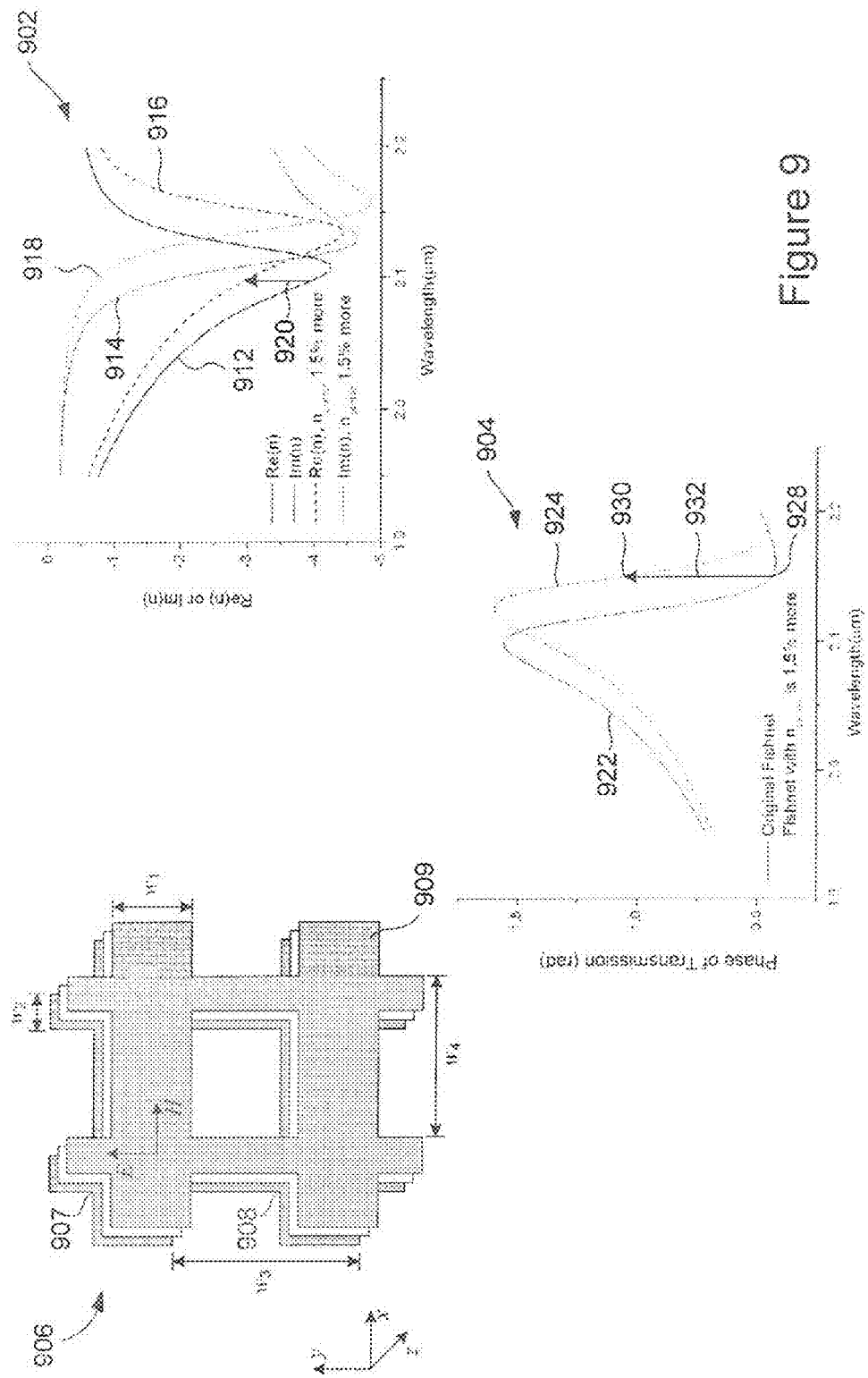
FIG. 9 shows a plot of the effective refractive index and phase changes for an exemplary negative index material fishnet configured and operated in accordance with embodiments of the present invention.

FIG. 9 shows a plot of the effective refractive index 902 and phase changes 904 for an exemplary fishnet 906 configured and operated in accordance with embodiments of the present invention. Plots 902 and 904 were obtained using the well-known finite element method ("FEM") by commercially available software COMSOL. FIG. 9 also includes parameters identifying the dimensions of the fishnet 906 used to obtain the results displayed in plots 902 and 904. The dimensions of the parameters are provided in Table I as follows:

TABLE I

| Parameter | Dimension |
| --- | --- |
| $w_1$ | 500 nm |
| $w_2$ | 100 nm |
| $w_3$ | 800 nm |
| $w_4$ | 800 nm |

The conductive layer 907 and 909 are composed of Au, and the intermediate layer 908 is composed of a dielectric material with a thickness of 60 nm whose dielectric constant is 1.5 when no electric signal is applied. The refractive index of the dielectric material can be modulated by varying applying appropriate electronic signals.

For electromagnetic radiation polarized in the y-direction and incident on the fishnet 906 in the z-direction, curves 912 and 914 of plot 902 represent the real and imaginary refractive index components, respectively, over a range of wavelengths with no electronic signal applied to conductive layers 907 and 909 of the fishnet 906. In the current wavelength range, of approximately 1.95 μm to approximately 2.2 μm, the fishnet 906 exhibits a negative effective refractive index with the largest negative refractive index occurring for incident electromagnetic radiation with wavelengths of approximately 2.1 μm. Curves 916 and 918 of plot 902 represent the real and imaginary refractive index components with a 1.5% change in the refractive index of the dielectric layer 908 when appropriate electronic signals are applied to the conductive layer 907 and 909 of the fishnet 906. Curve 916 exhibits a real negative refractive index shift for incident electromagnetic radiation with the largest negative refractive index occurring for incident electromagnetic radiation with wavelengths of approximately 2.1 μm. In other words, the fishnet 906 can be operated to change the effective refractive index that incident electromagnetic radiation encounters over particular wavelength ranges. For example, incident electromagnetic radiation with a wavelength of interest, such as a wavelength of approximately 2.1 μm, encounters the strongest real negative refractive index component when no electronic signal is applied to the conductive layers 907 and 909 of the fishnet 906. However, when appropriate electronic signals are applied to the conductive layers 907 and 909, the refractive index encountered by the wavelength of interest is shifted to a relatively smaller in magnitude refractive index, as indicated by directional arrow 920.

A change in the refractive index encountered by the wavelength of interest shifts the transmission phase of the wavelength of interest. Curves 922 and 924 of plot 904 represent the transmission phase of electromagnetic radiation over a range of wavelengths passing through the fishnet 906 for two different refractive indices of the intermediate layer 908. Curve 922 represents the transmission phase acquired by electromagnetic radiation over a range of wavelengths passing through the fishnet 906 when no electronic signal is applied to the fishnet 906. Curve 924 represents the transmission phase acquired by electromagnetic radiation over a range of wavelengths passing through the fishnet 906 when electronic signals applied to the conductive layers 907 and 909 of the fishnet 906 change the refractive index of the intermediate layer 908 by 1.5%. The fishnet 906 can be operated to shift the phase acquired by a wavelength of interest. The transmission phase is the phase acquired by electromagnetic radiation transmitted through the fishnet 906. For example, when no electronic signal is applied to the fishnet 906, point 928 indicates that electromagnetic radiation with the wavelength interest, approximately 2.15 μm, transmitted through the fishnet 906 acquires a transmission phase of approximately 0.45 radians. On the other hand, when electronic signals corresponding to the curve 924 are applied to the fishnet 906, the wavelength of interest acquires a transmission phase of approximately 1.05 radians represented by point 930, which is a transmission phase shift of approximately 0.6 radians from the point 928 to the point 930, as indicated by directional arrow 932.

Optical Resonators

Figure 10:
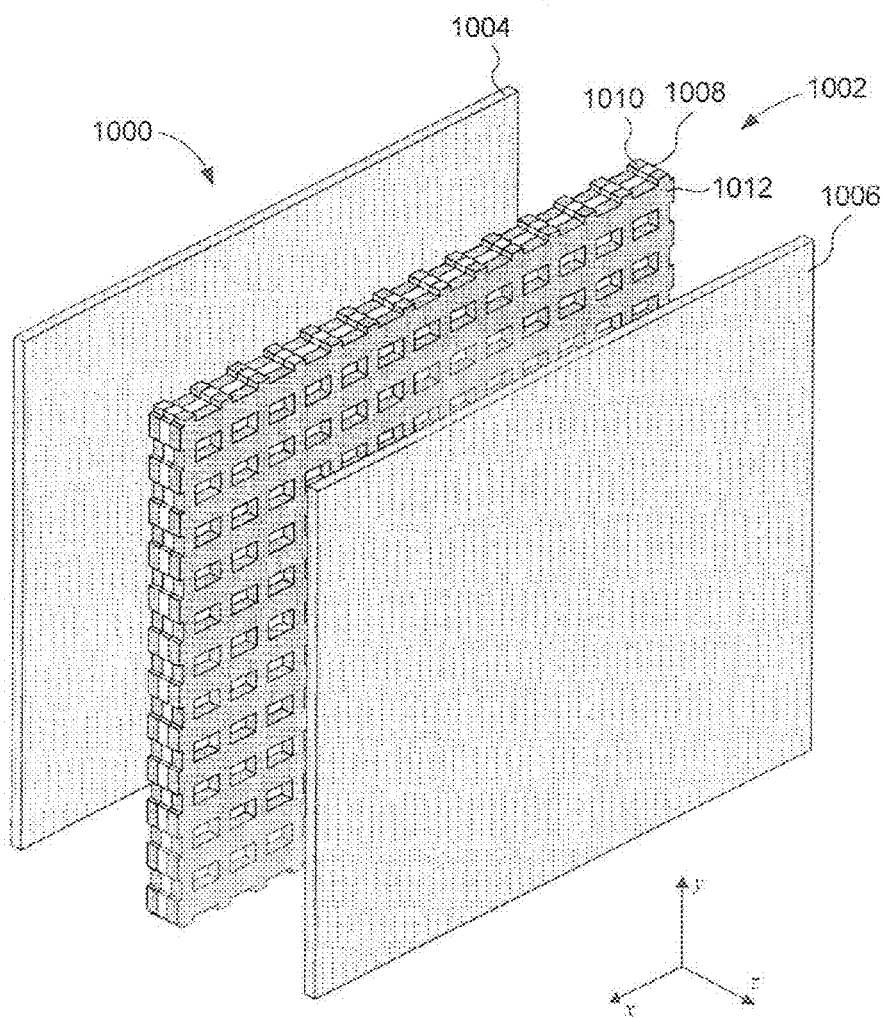
FIG. 10 shows a schematic representation and isometric view of a compact optical resonator 1000 configured in accordance with embodiments of the present invention.

FIG. 10 shows a schematic representation and isometric view of a compact optical resonator 1000 configured in accordance with embodiments of the present invention. The resonator 1000 comprises a fishnet 1002 disposed two approximately parallel reflective structures 1004 and 1006 that form a resonant cavity for appropriate wavelengths of electromagnetic radiation. As shown in FIG. 10, the fishnet 1002 is positioned approximately parallel to the reflective structures 1004 and 1006 with open space between the fishnet 1002 and the reflective structures 1004 and 1006. The fishnet 1002 comprises a dielectric layer 1008 sandwiched between two conducting layers 1010 and 1012 and, as shown in FIG. 10, the fishnet 1002 includes an array of approximately regularly spaced rectangular-shaped holes. In other embodiments, the holes can be square, elliptical, circular, irregularly shaped, or any other suitable shape for forming resonance structures, as described above in the Negative Index Material Fishnet subsection. The reflective structures 1004 and 1006 can be plates composed of Au, Ag, or any other suitable material for reflecting electromagnetic radiation.

Figure 11A:
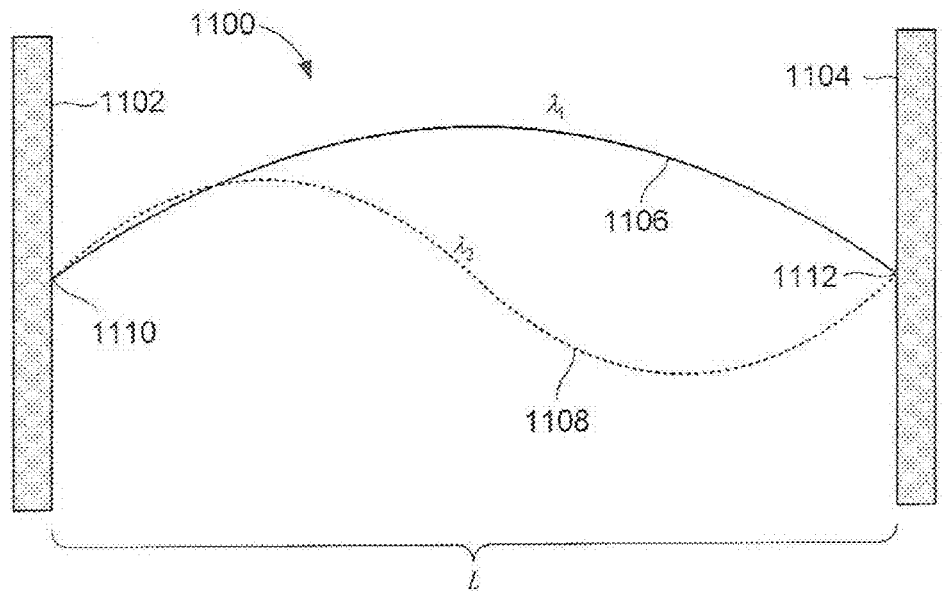
FIG. 11A shows a side view and schematic representation of a Fabry-Perot cavity.

The fishnet 1002 is configured and inserted into the cavity of the resonator 1000 so that the cavity length between the reflective structures 1004 and 1006 is less than half the fundamental wavelength supported by the optical resonator 1000. Consider first an optical resonator 1100, shown in FIG. 11A, that does not include a fishnet. The optical resonator 1100 comprises reflectance structures 1102 and 1104 of PEC mirrors with a cavity length L. Curves 1106 and 1108 represent just two standing electromagnetic waves with resonance wavelengths $\lambda_1$ and $\lambda_2$, respectively, resonating within the cavity. Each standing electromagnetic wave results from associated sinusoidal wave trains of the same wavelength moving in opposite directions, bouncing back and forth between the reflective structures 1102 and 1104 and interfering with each other. The cavity length L is the optical path length traveled by the resonating electromagnetic radiation. Nodes 1110 and 1112 correspond to reflections at the cavity boundaries with zero amplitude displacement. The nodes 1110 and 1112 form as a result of the sinusoidal wave trains having the same wavelength and adding with opposite phase to cancel each other out at the cavity boundaries. Curve 1106 represents the fundamental wavelength $\lambda_1$ of the resonator 1100 with the cavity length L equal to $\lambda_1/2$. In principle, the cavity length L cannot be shortened and still provide resonance for the fundamental wavelength $\lambda_1$. Curve 1106 is the second longest resonance wavelength $\lambda_2$ the resonator 1100 can support. Cavities with reflecting structures other than mirrors have similar properties. In other words, the length of the cavity is approximately half of the wavelength of the fundamental mode.

Figure 11B:
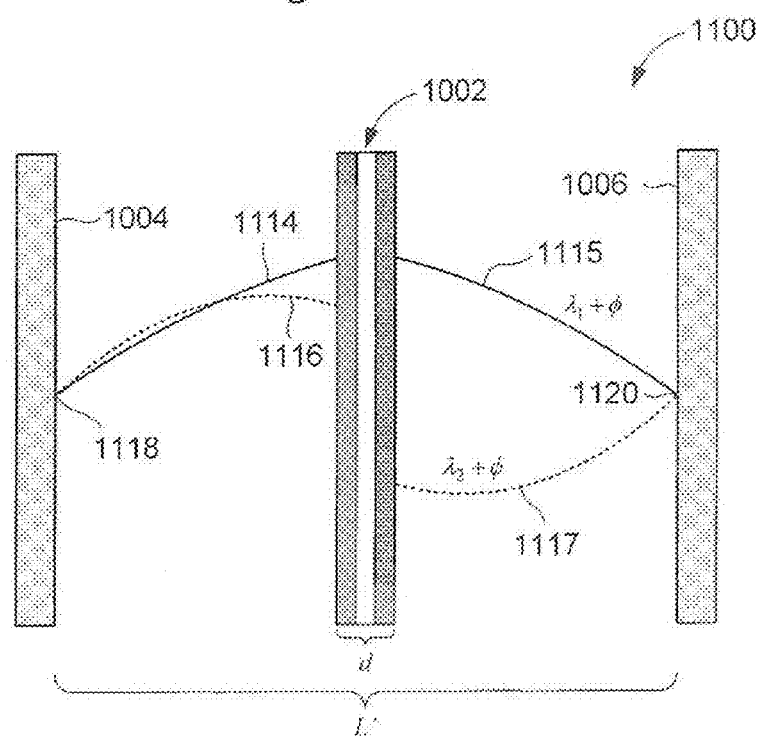
FIG. 11B shows a side view and schematic representation of the negative index material fishnet, shown in FIG. 10, operated in accordance with embodiments of the present invention.

On the other hand, embodiments of the present invention include inserting a fishnet into the cavity of a resonator and configuring the resonator with a the cavity length less than half the fundamental wavelength. For example, consider now FIG. 11B, which shows a side view of the compact optical resonator 1000 operated in accordance with embodiments of the present invention. The cavity length L' of the resonator 1000 is less than the cavity length L of the resonator 1100. In certain embodiments, the fishnet 1002 can be configured with a negative refractive index for the wavelengths $\lambda_1$ and $\lambda_2$. In other embodiments, the refractive index of the fishnet 1002 can be positive for the wavelengths $\lambda_1$ and $\lambda_2$. Curves 1114 and 1115 represent portions of the standing wave associated with the wavelength $\lambda_1$, and curves 1116 and 1117 represent portions of the standing wave associated with the wavelength $\lambda_2$. For the sake of simplicity, consider a case when the effective impedance of the fishnet equals that of free space. In this case, there is substantially no reflection at the surface of the fishnet, and the resonant condition can be completely determined by the phase delay the electromagnetic wave achieves in a round trip of the cavity. The sinusoidal wave trains acquire a transmission phase shift each time the waves pass through the fishnet 1002, bouncing back and forth between the reflective structures 1004 and 1006 and interfering with each other. The transmission phase shift introduced by the fishnet 1002 is negative, thus shortening the distance reflected and transmitted sinusoidal wave trains travel for destructive interference to occur at a cavity boundary. In other words, the optical path length ("OPL") of the cavity is given by:

$$OPL = (L' - d) - |n|d$$

where d is the thickness of the fishnet 1002, and |n| is the absolute value of the refractive index of the fishnet 1002. As shown in FIG. 11B, the cavity length L' is selected so that the transmission phase shifted sinusoidal waves bounce back and forth between the reflective structures 1004 and 1006 and add with opposite phase cancelling each other out at the cavity boundaries at nodes 1118 and 1120.

In the above discussing with reference to FIG. 11B, the fishnet 1002 is assumed to have an effective impedance that is approximately the same as that of free space. In practice, it is recognized that a fishnet can exhibit a resonant condition that is more complex, because reflections also exist at the surfaces of the fishnet. However, the conclusions described above with reference to FIG. 11B are similar. In other words, in practice, the fishnet can greatly reduce the length of the cavity.

In general, compact optical resonators configured in accordance with embodiments are subwavelength resonators that can support a fundamental wavelength greater than twice the length of the cavity. In other words, a compact optical resonator including a fishnet configured with a negative refractive index for the fundamental wavelength $\lambda_1$ and inserted into the cavity of the optical resonator with cavity length L' satisfies the condition:

$$L' = \frac{\lambda_1}{q}$$

where q is a number greater than 2.

In the above discussion, the reflective structures 1004 and 1006 of the resonator 1000 are assumed to have a reflectivity of magnitude "1." In other words, for the sake of simplicity of discussion, the resonator 1000 is isolated, which simplifies the discussion and understanding of the operation of the resonator 1000. However, in practice, it is recognized that when the resonator is implemented in a filter or as a modulator or in any other implementation, the reflectivity of the reflective structures 1004 and 1006 have a magnitude of reflectivity of approximately 1. For an incident electromagnetic wave with a resonance wavelength of the cavity, the resonant mode builds up inside the cavity, so that the transmission is maximized. Otherwise, the transmission is small.

Figure 12A:
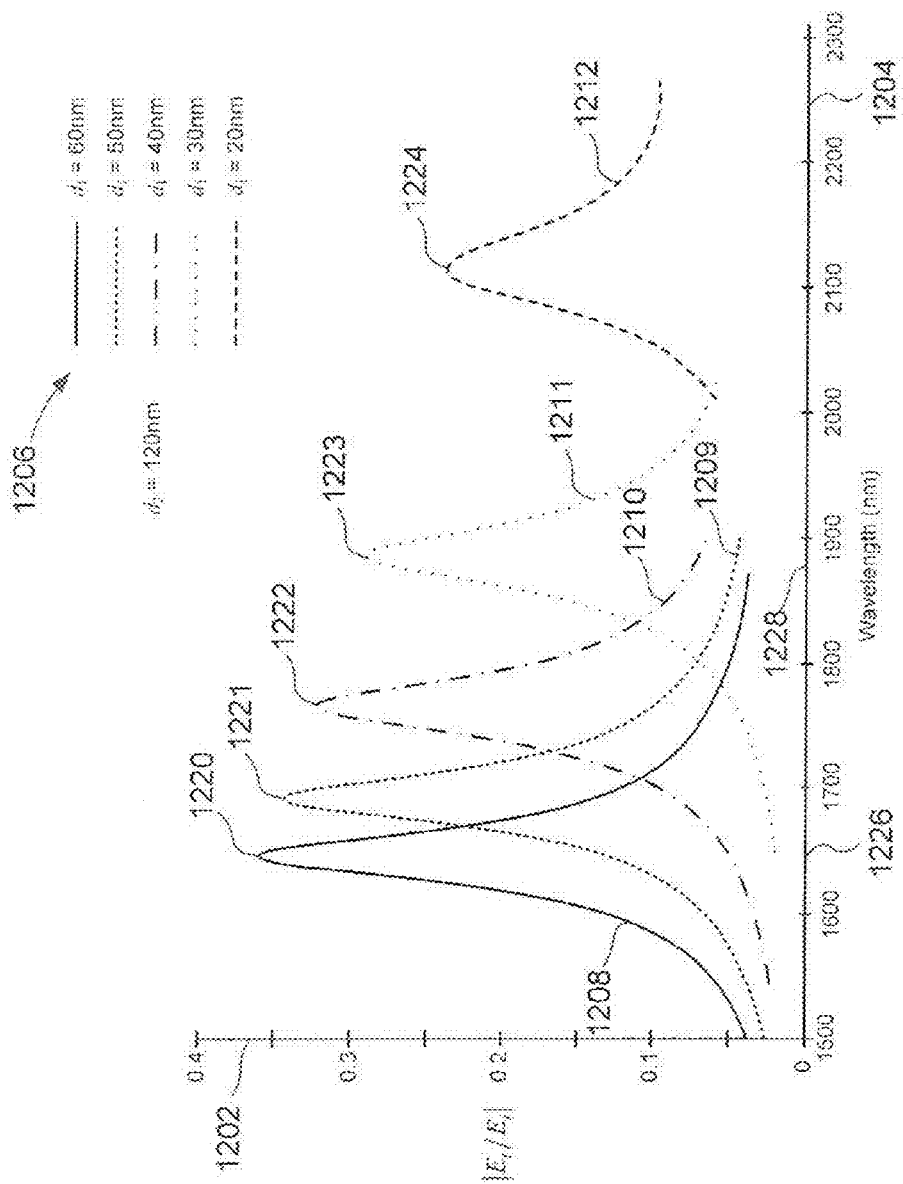
FIG. 12A shows a transmittance versus wavelength plot for an exemplary compact optical resonator configured and operated in accordance with embodiments of the present invention.
Figure 12B:
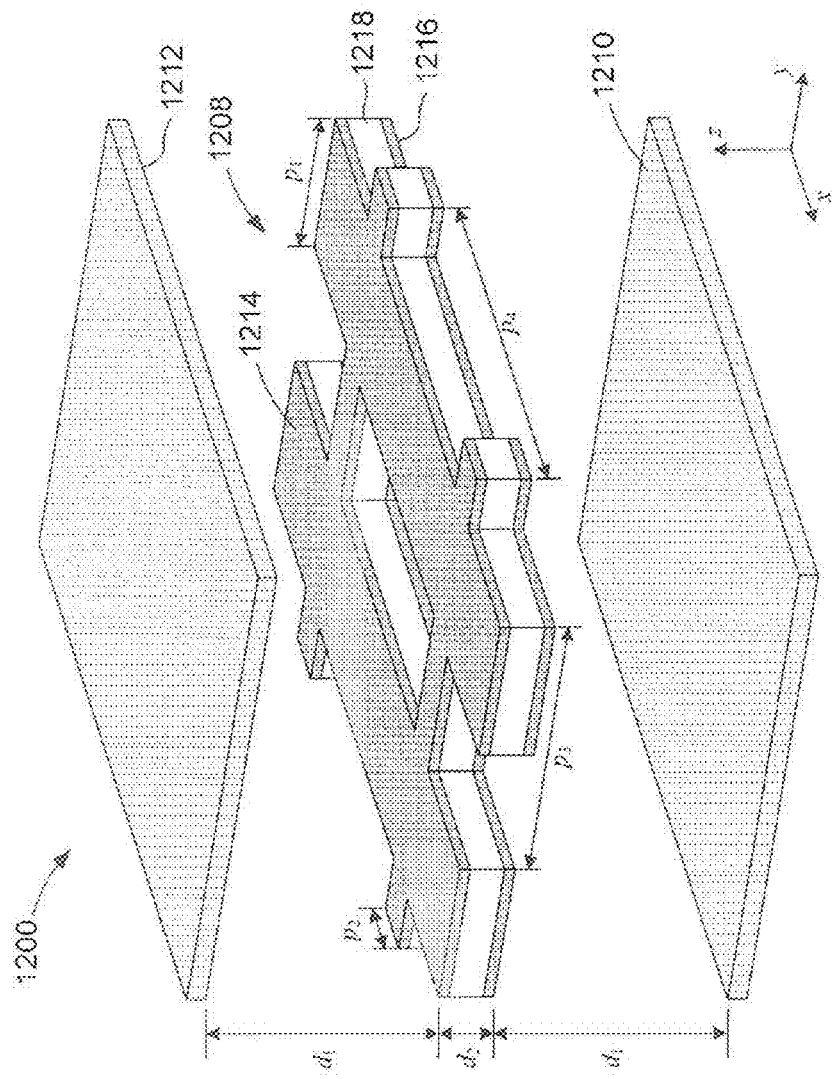
FIG. 12B shows an isometric view of compact optical resonator configured in accordance with embodiments of the present invention.

FIGS. 12A-12B show simulation results that demonstrate the subwavelength capabilities of compact optical resonators configured in accordance with embodiments of the present invention. FIG. 12A shows a transmittance versus wavelength plot for an exemplary compact optical resonator 1200, shown in FIG. 12B, configured and operated in accordance with embodiments of the present invention. In FIG. 12A, axis 1202 represents transmittance, $|E_t/E_i|$, where $E_i$ is the amplitude of electromagnetic radiation incident upon the resonator 1200 with propagating direction perpendicular to the surface of the cavity, and $E_t$ is the amplitude of electromagnetic radiation transmitted from the resonator 1200. Axis 1204 represents a range of wavelengths in the electromagnetic spectrum. FIG. 12A also includes a legend 1206 of parameter dimensions associated with the resonator 1200. As shown in FIG. 12B, parameter $d_2$ corresponds to the thickness of the fishnet 1208, and the parameter $d_1$ corresponds to the distance between a surface of the fishnet 1208 and cavity surfaces formed by the reflectance structures 1210 and 1212. FIG. 12B also includes parameters identifying the dimensions of the fishnet 1208 used to obtain the results displayed in FIG. 12A. The dimensions of the parameters are provided in Table II as follows:

TABLE II

| Parameter | Dimension |
|---|---|
| $p_1$ | 500 nm |
| $p_2$ | 100 nm |
| $p_3$ | 800 nm |
| $p_4$ | 800 nm |

The conductive layers 1214 and 1216 are 30 nm thick and composed of Au, the intermediate layer 1218 is 60 nm thick and composed of $SiO_2$, and the reflective structures are 20 nm thick and composed Au. Electromagnetic radiation resonating in the cavity is polarized in the y-direction and propagates in the z-direction. Returning to FIG. 12A, curves 1208-1212 each represent transmittance over a different range of wavelengths. Each curve is identified by a different line pattern that corresponds to a distance $d_1$ displayed in the legend 1206. For example, curve 1208 corresponds to a distance $d_1$ of 60 nm. Curves 1208-1212 were obtained using the well-known finite element method ("FEM") by a commercially available software COMSOL.

In FIG. 12A, peaks 1220-1224 of curves 1208-1212 correspond to the fundamental wavelengths having resonance in the optical resonator 1200 with the associated distances listed in the legend 1206. The factor q associated with each of the peaks 1220-1224 is greater than 2. For example, peak 1220 corresponds to a fundamental wavelength $\lambda_1$ equal to 1650 nm 1226, when the resonator 1200 is configured with a cavity length:

$$L' = 2(60 \text{ nm}) + 120 \text{ nm} = 240 \text{ nm}$$

The cavity length of 240 nm is considerably shorter than half the fundamental wavelength of 1650 nm as indicated by:

$$L' = 240 \text{ nm} < \frac{1650 \text{ nm}}{2} = 825 \text{ nm}$$

where in this case, q is approximately 6.875. As another example, peak 1223 corresponds to a fundamental wavelength $\lambda_1$ equal to 1880 nm 1228, when resonator 1200 is configured with a cavity length:

$$L' = 2(30 \text{ nm}) + 120 \text{ nm} = 180 \text{ nm}$$

The cavity length 180 is again considerably shorter than half the fundamental wavelength 1880 nm as indicated by:

$$L' = 180 \text{ nm} < \frac{1880 \text{ nm}}{2} = 940 \text{ nm}$$

where in this case, q is approximately 10.4.

By comparison, FIG. 13 shows a plot of a transmission curve 1302 versus wavelength for a Fabry-Perot cavity 1304 comprising the same Au reflective structures 1210 and 1212, but with the fishnet 1208 removed. The cavity length L is 932 nm and the peak 1306 occurs at a fundamental wavelength of approximately 2000 nm 1308. Thus, the Fabry-Perot cavity 1304 provides resonance for a fundamental wavelength that is approximately twice the length of the cavity. Note the curve 1302 was obtained for the cavity 1304 using the same FEM method cited above.

Figure 14:
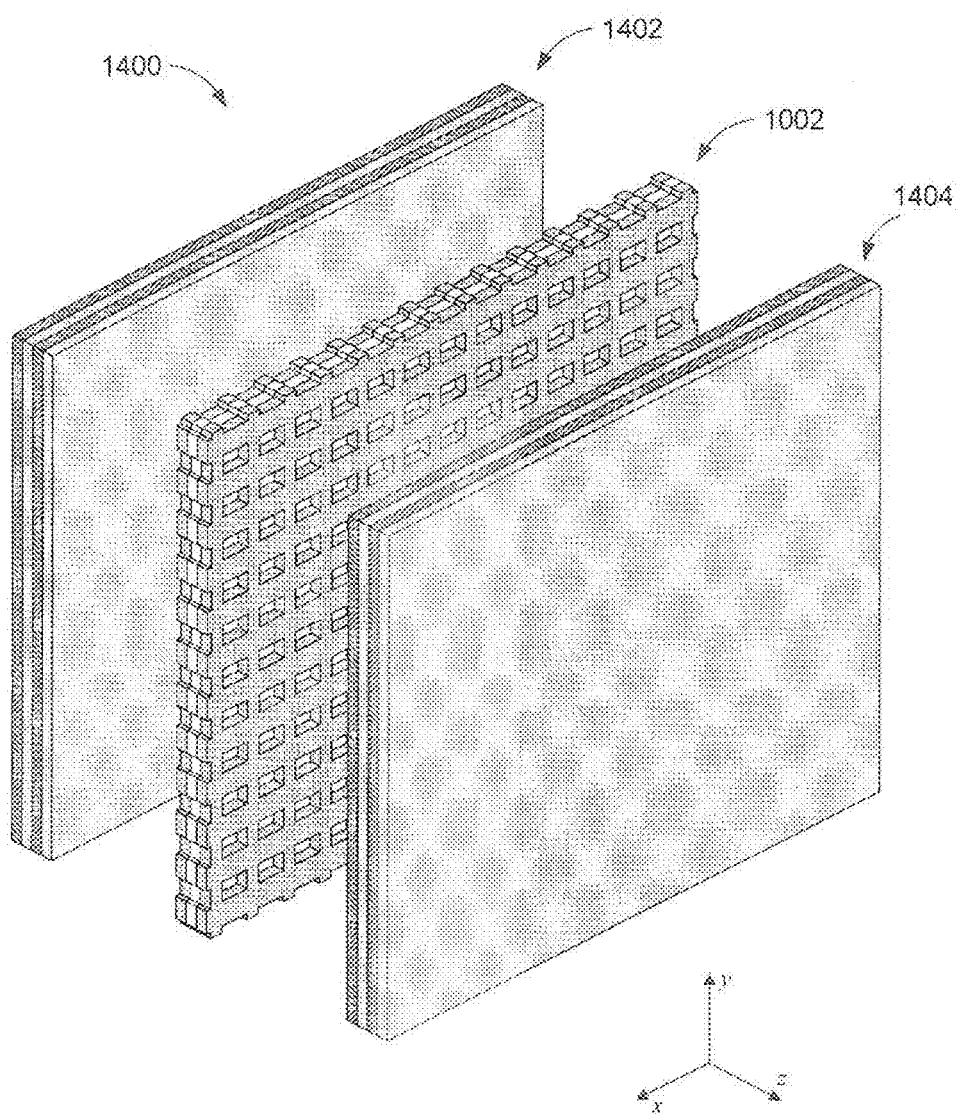
FIG. 14 shows an isometric view and schematic representation of an optical resonator configured in accordance with embodiments of the present invention.

In other embodiments, the reflective structures 1004 and 1006 of the resonator 1000 can be Bragg mirrors. FIG. 14 shows an isometric view and schematic representation of an optical resonator 1400 configured in accordance with embodiments of the present invention. The resonator 1400 includes the same fishnet 1002, but the reflective structures 1004 and 1006 are replaced by Bragg mirrors 1402 and 1404. The Bragg mirrors 1102 and 1104 can be configured to reflect and trap electromagnetic radiation with operating wavelengths as described above with reference to FIGS. 10-12.

Figure 15:
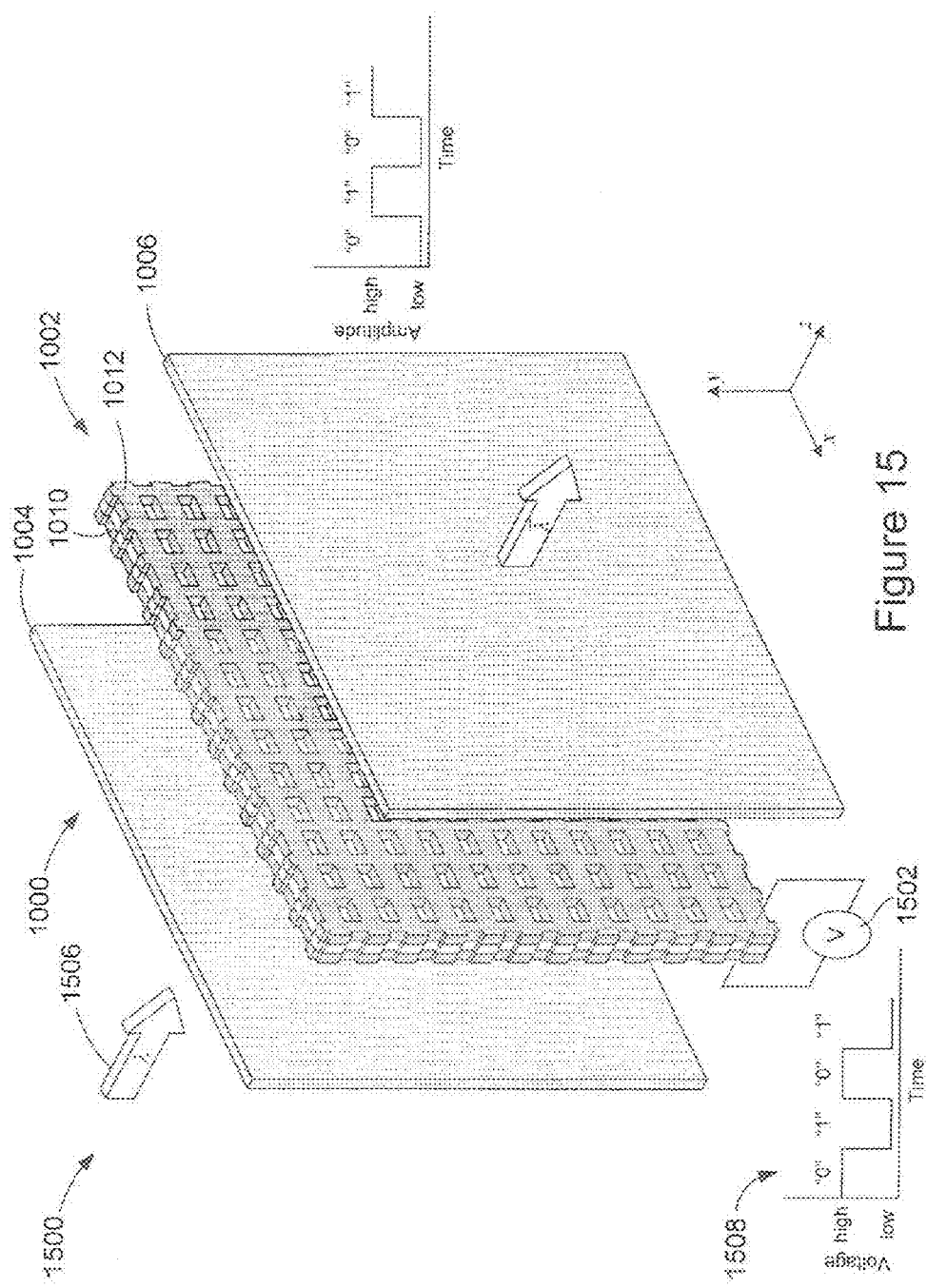
FIG. 15 shows an isometric view and schematic representation of an optical modulator configured in accordance with embodiments of the present invention.

Embodiments of the present invention include optical modulators comprising an optical resonator, such as optical resonators 1000 and 1400, with the conductive layers of the fishnet in electronic communication with an electronic signals source, such as a voltage or a current source. FIG. 15 shows an isometric view and schematic representation of an optical modulator 1500 configured in accordance with embodiments of the present invention. The modulator 1500 comprises the resonator 1000 and a voltage source 1502 in electronic communication with the conductive layers 1010 and 1012 of the fishnet 1002. The optical modulator 1500 can be configured so that when no voltage is applied to the conductive layers 1010 and 1012 the wavelength $\lambda$ of an incident beam of unmodulated electromagnetic radiation 1506 resonates within the cavity, as described above with reference to FIG. 12B. When a voltage is applied to the conductive layers 1010 and 1012, the optical property of the fishnet 1002 changes, so does its effective refractive index, and the incident radiation is no longer resonant and the electromagnetic radiation entering the cavity is destroyed by destructive interference. As a result, little to no electromagnetic radiation is emitted from the resonator.

An electronic signal encoding binary information in relatively high and low voltages that are applied to the conductive layers 1010 and 1012 encodes the same information in the amplitude of electromagnetic radiation emitted from the resonator. For example, FIG. 15 includes a plot 1508 of a four-bit voltage pattern applied to the conductive layers 1010 and 1012, where a high voltage represents binary "0" and a low or no voltage represents binary "1." Changes in the optical properties, such as the effective refractive index, of the fishnet 1002 correspondingly shift the resonator 1000 in and out of resonance. The electromagnetic signal $\bar{\lambda}$ emitted from the resonator comprises high and low amplitudes where a relatively low amplitude represents binary "0" and corresponds to a high voltage of the electronic signal, and a relatively high amplitude represents binary "1" and corresponds to a low voltage of the electronic signal.

In other embodiments, the fishnet 1002 can be configured so that the resonator is resonant with the unmodulated wavelength when a relative high voltage is applied to the conductive layers 1010 and 1012 and off resonance when a low or no voltage is applied to conductive layers 1010 and 1012. Thus, the electromagnetic signals emitted from the resonator comprises high and low amplitudes where a relatively low amplitude represents binary "0" corresponds to a low voltage of the electronic signal, and a relatively high amplitude represents binary "1" corresponds to a high voltage of the electronic signal.

Figure 16:
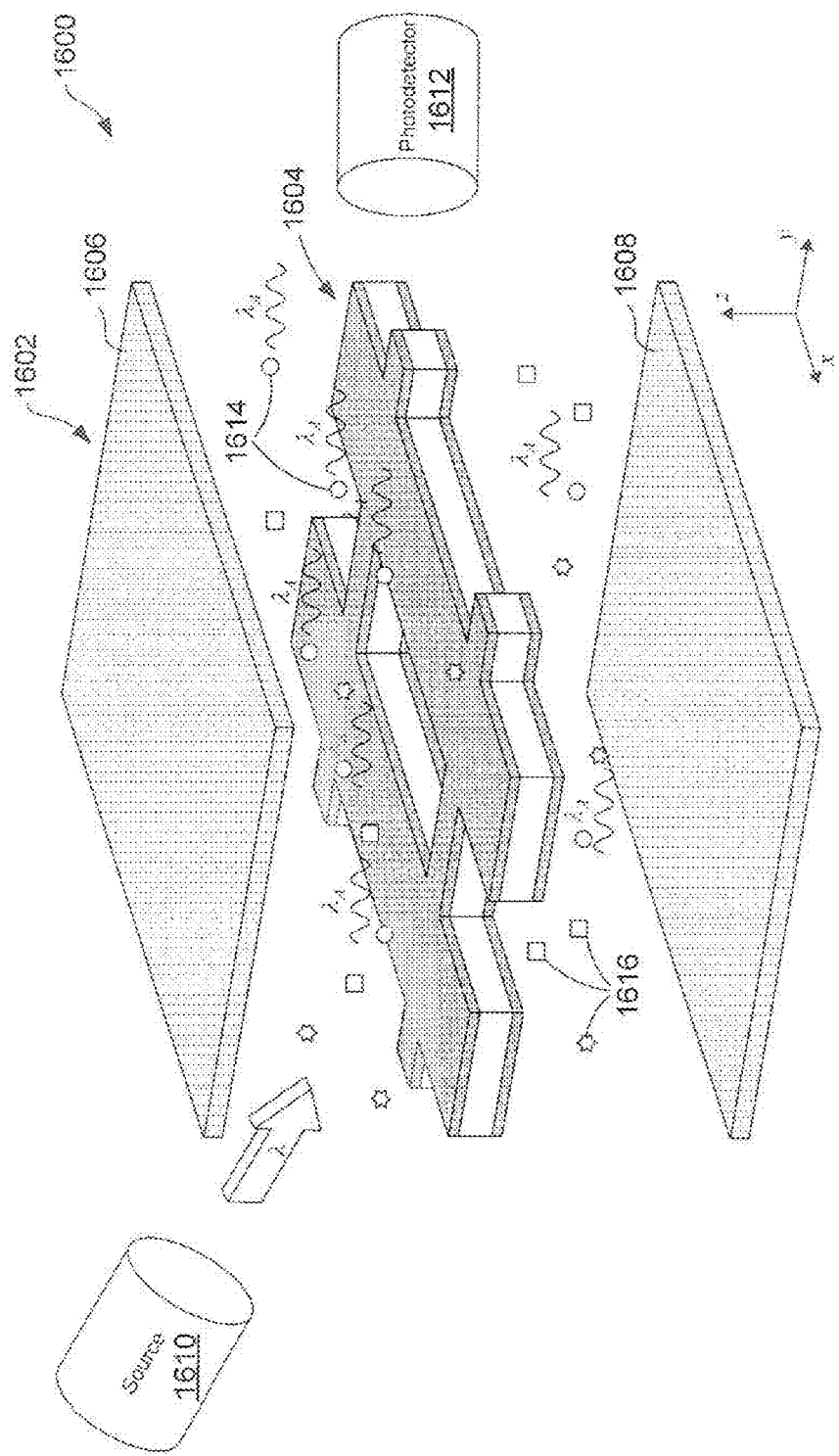
FIG. 16 shows an isometric view and schematic representation of an optical sensor configured in accordance with embodiments of the present invention.

Embodiments of the present invention also include optical sensors comprising optical resonators configured in accordance with embodiments of the present invention. FIG. 16 shows an isometric view and schematic representation of an optical sensor 1600 configured in accordance with embodiments of the present invention. The optical sensor 1600 comprises an optical resonator 1602 that includes a fishnet 1604 disposed between two reflective structures 1606 and 1608, as described above with reference to FIG. 10. The sensor 1600 also includes an electromagnetic radiation source 1610 and a photodetector 1612.

As shown in FIG. 16, a material containing an analyte 1614 is input to the cavity between the reflective structures 1606 and 1608. The material may also include other compounds 1616. The source 1610 can be configured to emit electromagnetic radiation $\lambda$ that electronically excites the analyte to emit relatively lower energy, longer wavelength radiation represented by $\lambda_A$. The photodetector 1612 can be positioned to detect the emitted radiation $\lambda_A$. Note, depending on the chemical composition of the analyte, the source 1610 may emit more than one wavelength of excitation energy, and the analyte 1614 may emit spectrum of radiation comprising one or more wavelengths that is unique to the analyte 1614. Detection of the spectrum is used to identify the presences of the analyte 1614.

In one embodiment, the fishnet 1604 can be configured and the cavity length dimensioned to resonate with and reinforce the excitation radiation $\lambda$, as described above with reference to FIGS. 11-12. As a result, more excitation electromagnetic radiation is available for electronic interaction with the analyte 1614.

In other embodiments, the fishnet 1604 can be configured and the cavity length dimensioned to resonate with and reinforce the emitted radiation $\lambda_A$. This type of reinforcement increases the likelihood of detecting radiation emitted from the analyte 1614 in cases where the analyte 1614 concentration is relative low.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purposes of illustration and description. They are not intended to be exhaustive of or to limit the invention to the precise forms disclosed. Obviously, many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents:

The invention claimed is:

1. An optical sensor comprising:
   an optical resonator including:
      two approximately parallel reflective structures positioned to form a resonant cavity, and
      a fishnet structure disposed within the cavity and oriented approximately parallel to the reflective structures;
   an electromagnetic radiation source positioned to emit electromagnetic radiation of a first wavelength into the cavity of the optical resonator, the first wavelength selected to electronically excite analyte molecules input to the cavity; and
   a photodetector positioned to detect a second wavelength of electromagnetic radiation emitted from the analyte molecules and output from the cavity of the optical resonator.

2. The optical sensor of claim 1 wherein the cavity length is dimensioned to support resonance for the first wavelength and the fishnet structure is configured for the first wavelength such that the first wavelength resonates within the cavity.

3. The optical sensor of claim 1 wherein the cavity length is dimensioned to support resonance for the second wavelength and the fishnet structure is configured for the second wavelength such that the second wavelength resonates within the cavity.

4. The optical sensor of claim 2 wherein the fishnet structure further comprises:
   a first conductive layer;
   a second conductive layer; and
   an intermediate layer sandwiched between the first and second conductive layers, wherein the fishnet structure includes an array of approximately regular spaces holes, each hole extending through the first and second layers and the intermediate layer.

5. The optical resonator of claim 2 wherein the reflective structures further comprise Bragg mirrors configured to reflect the electromagnetic radiation having the fundamental wavelength.

6. The optical resonator of claim 2 wherein the reflective structures further comprises a reflective material.

7. A modulator comprising:
   an optical resonator including:
      two approximately parallel reflective structures positioned to form a resonant cavity, and a fishnet structure disposed within the cavity and oriented approximately parallel to the reflective structures; and
      an electronic signal source electronically coupled to the fishnet wherein data is encoded in a beam of unmodulated electromagnetic radiation input the resonant cavity by applying electronic signals to the fishnet structure, such that the electronic signals change the optical property of the fishnet, shifting resonance of the resonant cavity.

8. The optical sensor of claim 7 wherein the cavity length is dimensioned to support resonance with the unmodulated electromagnetic radiation and the fishnet structure is configured for the unmodulated electromagnetic when no electronic signal is applied.

9. The optical sensor of claim 7 wherein the cavity length is dimensioned to support resonance with the unmodulated electromagnetic radiation and the fishnet structure is configured for the unmodulated electromagnetic when the electronic signal is applied.

10. The optical sensor of claim 7 wherein the fishnet structure further comprises:
    a first conductive layer;
    a second conductive layer; and
    an intermediate layer sandwiched between the first and second conductive layers, wherein the fishnet structure includes an array of approximately regular spaces holes, each hole extending through the first and second layers and the intermediate layer.

11. The optical resonator of claim 10 wherein the reflective structures further comprise Bragg mirrors configured to reflect the electromagnetic radiation having the fundamental wavelength.

12. The optical resonator of claim 10 wherein the reflective structures further comprises a reflective material.

13. The optical resonator of claim 7 wherein the electronic signal source can be voltage source or a current source.

* * * * *